United States Patent [19]
Baum et al.

[11] Patent Number: 6,018,065
[45] Date of Patent: Jan. 25, 2000

[54] METHOD OF FABRICATING IRIDIUM-BASED MATERIALS AND STRUCTURES ON SUBSTRATES, IRIDIUM SOURCE REAGENTS THEREFOR

[75] Inventors: Thomas H. Baum, New Fairfield; Chong-Ying Xu, New Milford, both of Conn.

[73] Assignee: Advanced Technology Materials, Inc., Danbury, Conn.

[21] Appl. No.: 08/966,797

[22] Filed: Nov. 10, 1997

[51] Int. Cl.[7] .................................................. C07F 15/00
[52] U.S. Cl. ............................. 556/136; 556/137; 556/9; 556/13; 556/16
[58] Field of Search .................... 556/9, 13, 16, 556/136, 137

[56] References Cited

U.S. PATENT DOCUMENTS

| | | | |
|---|---|---|---|
| 5,763,633 | 6/1998 | Vaartstra | 556/136 |
| 5,840,897 | 11/1998 | Kirklin | 546/2 |

OTHER PUBLICATIONS

CA:98:63195 abs of J Chem Soc Dalton Trans by Brouwers (9) pp. 1777–1782, 1982.

Gmelin acc No. 751803 abs of J Chem Soc Dalton by Hitchcock pp. 1295–1302, 1985.

JP 08–260148 A (Fujitsu Ltd) Oct. 8, 1996, col. 2, lines 10–20, col. 6, lines 30–50, Figure 7.

Database Caplus on STN, American Chemical Society (Washington, DC, USA) Accession No. 1983:63195, Brouwers et al., 'Photochemistry of acetylacetonato–, trifluoroacetylacetonato–, and hexafluoracetylacetonatodicarbonylrhodium and —iridium complexes in frozen gas mixtures at 12 K', abstract, University of Amsterdam, Sep., 1982.

Hitchcock et al., Fluorophosphine Complexes of Rhodium(I) and Iridium(I). J. Chem. Soc. Dalton Trans. Jul., 1985, pp. 1295–1301, especially p. 1297.

Gerfin et al., Groth of Iridium Films by metal organic Chemical Vapor Deposition, Thin Solid Films, Apr. 1994, pp. 352–355.

Leipoldt, et al., "Kinetics of the Substitution Reactions of β—Diketonato–1,5–Cyclo–Octadieneiridium(I) Complexes with Derivatives of 1, 10–Phenanthroline and 2,2'–Dipyridyl," Journal of Organometallic Chemistry, 418, (1991), pp. 241–247.

Sasson, et al., "Bromide Catalysis in the Oxidative Addition of Iodomethane to Iridium(I) Complexes," Inoraganica Chimica Acta. 173 (1990) pp. 155–158.

Advanced Inorganic Chemistry by Cotton and Wilkinson p. 772, 1972.

*Primary Examiner*—Paul J. Killos
*Assistant Examiner*—Jean F. Vollano
*Attorney, Agent, or Firm*—Steven J. Hultquist; Oliver A.M. Zitzmann

[57] ABSTRACT

A method of forming an iridium-containing film on a substrate, from an iridium-contaiing precursor thereof which is decomposable to deposit iridium on the substrate, by decomposing the precursor and depositing iridium on the substrate in an oxidizing ambient environment which may for example contain an oxidizing gas such as oxygen, ozone, air, and nitrogen oxide. Useful precursors include Lewis base stabilized Ir(I) β-diketonates and Lewis base stabilized Ir(I) β-ketoiminates. The iridium deposited on the substrate may then be etched for patterning an electrode, followed by depositing on the electrode a dielectric or ferroelectric material, for fabrication of thin film capacitor semiconductor devices such as DRAMs, FRAMs, hybrid systems, smart cards and communication systems.

14 Claims, No Drawings

METHOD OF FABRICATING IRIDIUM-BASED MATERIALS AND STRUCTURES ON SUBSTRATES, IRIDIUM SOURCE REAGENTS THEREFOR

CROSS-REFERENCE TO RELATED APPLICATION

This application is concurrently filed with U.S. patent application Ser. No. 08/966,796 filed Nov. 10, 1997 in the names of Thomas H. Baum and Frank Dimeo, Jr. for "Iridium-Based Electrode Structures, and Method of Making the Same," the disclosure of which hereby is incorporated herein in its entirety.

BACKGROUND OF TV INVENTION

1. Field of the Invention

This invention relates to a method of forming iridium- or iridium-containing materials on substrates, such as Ir-based electrode structures for microelectronic devices and subassemblies, as well as to Ir source reagent materials, and novel dielectric capacitor or ferroelectric material structures.

2. Description of the Related Art

Iridium (Ir) and iridium oxide ($IrO_2$) are of great interest for use as electrode materials in both dynamic random access memories (DRAMs) and for ferroelectric-based memory devices (FRAMs) which incorporate perovskite metal oxide thin-films as the capacitor layer.

The advantages of Ir over other possible electrode materials include ease of deposition, the ability to "dry etch" the material, the ability to form a stable conducting oxide at high temperatures in an oxidizing environment, and the ability to operate stably at high temperatures in a working device.

The deposition and processing of Ir-based electrodes is highly desirable in view of the aforementioned advantages. Further, the formation of $IrO_2$ acts as a diffusion barrier to oxidation of conducting polysilicon vias or plugs, as is required in high density DRAM or FRAM devices.

Based on the need for Ir-based electrodes, the art has continued to seek improvements in source materials and deposition techniques for the formation of Ir-based films.

The art has variously disclosed the chemical vapor deposition of iridium for the manufacture of electronic devices in a reducing atmosphere, such as hydrogen gas environment. The art has taught the use of such reducing atmosphere for the purpose of achieving the deposition of element metal iridium for electrodes in applications in which high temperature dielectric materials (e.g., SBT, BST, PZT, PLZT, PNZT, $LaCaMnO_3$, etc., wherein SBT=strontium bismuth tantalate, BST=barium strontium titanate, PZT=lead zironium titanate, PLZT=lead lanthanum zirconium titanate, PNZT=lead niobium zirconium titanate) are deposited on the electrode, to minimize the possibility of degradation of the dielectric in such applications and to concurrently achieve the formation of high purity metal.

The art has especially sought improvements in process technology for the formation of semiconductor and ferroelectric structures which employ Ir electrodes specifically associated with complex dielectric or ferroelectric material layers as thin-film capacitors.

It is an object of the present invention to provide novel source reagents and a process for the formation of iridium-based electrodes that achieve a material simplification in fabrication efficiency and cost, and provide an electrode structure that is highly advantageous for integration with silicon device technology, being efficient and readily fabricated.

It is another object of the invention to provide a simplified method for the fabrication of metal oxide thin film capacitor structures including iridium, iridium oxide or iridium-containing electrode elements, as metal contacts for the oxide DRAM and FRAM devices.

Other objects and advantages of the present invention will be more fully apparent from the ensuing disclosure and appended claims.

SUMMARY OF THE INVENTION

This invention relates to a method of forming iridium- or iridium-containing materials on substrates, such as Ir-based electrode structures for microelectronic devices and subassemblies, and catalytic materials, as well as to Ir source reagent materials, and novel dielectric material structures.

As used herein, the term "Ir-based" or "iridium-based" refers broadly to elemental iridium, iridium oxide and iridium-containing material compositions.

The present invention also relates to novel high temperature dielectric or ferroelectric thin film capacitor structures including Ir-based electrode elements.

In one aspect, the invention relates to a method of forming an iridium-containing film on a substrate, from an iridium-containing precursor thereof which is decomposed to deposit iridium on the substrate, such method comprising decomposing the precursor and depositing iridium on the substrate in an oxidizing ambient environment. The deposition of iridium on the substrate may be carried out in any suitable manner and by any appropriate techniques of the art, including chemical vapor deposition (CVD), assisted CVD, or physical deposition methods such as ion plating, rapid thermal processing, molecular beam epitaxy, etc.

As used herein, the term "oxidizing ambient environment" means an environment including oxygen-containing gas, such as oxygen, ozone, air, nitrogen oxide ($NO_x$), or the like. Such oxidizing atmosphere may be provided in a deposition chamber or reaction vessel in which the deposition is carried out, and enables the formation of iridium or iridium oxide on the substrate. Accordingly, the deposition may be conducted in an ambient air environment, thereby simplifying the formation of the iridium-containing film on the substrate. In an alternate embodiment, $IrO_2$ may be formed in a post-deposition process from Ir metal by treatment in an oxidizing environment.

The Ir precursor material may be of any suitable composition and type. In preferred practice of the present invention, the precursor may suitably comprise a Lewis base-stabilized β-diketonate iridium composition or a Lewis base-stabilized beta-ketoiminate composition, as hereafter more fully described.

When the iridium-containing film is employed to form an electrode or other patterned structure on the substrate, the deposited iridium or iridium oxide film may be dry etched with a halogen-based plasma and/or preferably, $XeF_2$, as more fully described in concurrently filed U.S. patent application Ser. No. 08/966,796 filed Nov. 10, 1997 in the names of Thomas H. Baum and Frank Dimeo, Jr. for "Iridium-Based Electrode Structures, and Method of Making the Same," the disclosure of which hereby is incorporated herein in its entirety. In such dry etching of a deposited iridium or iridium oxide film, the etch rates can optionally be enhanced through the use of Lewis-based adducts or electron back-bonding species such as carbon monoxide, trifluorophosphine, or trialkylphosphines.

In yet another aspect of the present invention, the iridium-containing film subsequent to its formation as an electrode structure may have deposited thereon a high temperature dielectric and/or ferroelectric material. An oxidizing ambient environment may be employed for the deposition of the iridium-containing film or may be used solely during the deposition of the oxide dielectric/ferroelectric.

It may therefore be unnecessary to purge the chamber of a reducing atmosphere, or to transfer the substrate article bearing the iridium-containing film from the iridium deposition chamber to a dielectric/ferroelectric deposition chamber, as has been done in the prior art to accommodate the usage of hydrogen or other reducing gas (forming gas) atmospheres in the iridium electrode formation step.

The method of this invention therefore achieves a substantial simplification of the procedure for forming a capacitor or other microelectronic device in which the iridium-containing electrode is overcoated with a dielectric or ferroelectric material.

Another aspect of the invention relates to a microelectronic device structure comprising an iridium oxide electrode element overcoated by a high temperature dielectric, e.g., SBT, PZT, BST, PLZT, PNZT, $LaCaMnO_3$, etc., wherein the electrode is conductively operative in relation to the high temperature dielectric. As used herein, high temperature dielectric refers to a dielectric material deposited on the electrode at a temperature above about 300° C. By way of example, dielectric films of lead zirconium titanate (PZT) are typically deposited at temperatures on the order of 500–600° C.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The present invention relates to the discovery that Ir-based electrode structures can be readily formed without the necessity of depositing the Ir component from a precursor or source material in a reducing atmosphere, as has heretofore been the approach and objective of the prior art.

Contrariwise, the present invention contemplates a method of forming an iridium-containing film on a substrate, from an iridium-containing precursor thereof which is decomposed to deposit iridium on the substrate, in which the decomposition of the precursor and the deposition of iridium on the substrate is carried out in an oxidizing ambient environment to deposit iridium in the form of iridium per se or in the form of iridium oxide.

Iridium may be deposited on the substrate in the method of the present invention in any suitable manner, including chemical vapor deposition, liquid delivery, sputtering, ablation, or any other suitable technique known in the art for deposition of metal on a substrate from a metal-organic or other precursor or source material. Among the foregoing, chemical vapor deposition is preferred when the iridium-based structures being formed have critical dimensions below about 0.5 microns.

In the method of the invention, the precursor for the iridium component may be any suitable iridium precursor compound, complex or composition which is advantageous for yielding iridium for deposition on the substrate. The iridium precursor may for example comprise a Lewis base-stabilized P3-diketonate iridium composition or a Lewis base-stabilized β-ketoiminate composition, of the formulae:

Lewis base stabilized Ir(I) β-diketonates of formula I:

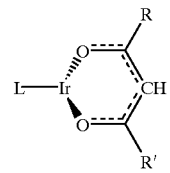

wherein R and R' are the same or different and may be H, aryl, perfluoroaryl, $C_1$–$C_6$ alkyl, or $C_1$–$C_6$ perfluoroalkyl, and L is a coordinating Lewis base, preferably alkene, diene, cycloalkene, cyclodiene, cyclooctatetraene, alkyne, substituted alkyne (symmetrical or asymmetrical), amnine, diamine, triamine, tetraamine, ether, diglyme, triglyme, tetraglyme, phosphine, carbonyl, dialkyl sulfide, vinyltrimethylsilane, and allyltrimethylsilane, or Lewis base stabilized Ir(I) β-ketoiminates of formula II:

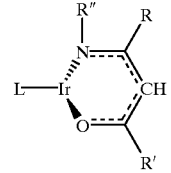

wherein R, R', and R" are the same or different, and are independently selected from the group consisting of H, aryl, perfluoroaryl, $C_1$–$C_6$ alkyl, or $C_1$–$C_6$ perfluoroalkyl, and L is a coordinating Lewis base, preferably selected from the group consisting of alkene, diene, cycloalkene, cyclodiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane, and allyltrimethylsilane.

For the Lewis base in the above precursors of formulae I and II, one or more Lewis base molecules may be preferred, especially for ether, alkene, alkyne, carbonyl and phosphine ligands. In some embodiments of precursors of formula II, R and R' may be identical and R" will be independently selected from the substituents listed above.

In CVD-based embodiments of the present invention, either a bubbler or organic solution liquid delivery can be utilized for the chemical vapor deposition of the $Ir/IrO_2$ thin film. The specific precursor may be suitably optimized for the delivery and transport of the precursor to the CVD reactor. The precursor is decomposed in the presence of an oxidant (e.g., $O_2$, $O_3$, or $N_2O$) to preferentially deposit the metal Ir (<500° C.) or the oxide, $IrO_2$ (>550° C.). In some applications, the formation of a bi-layered $Ir/IrO_2$ film may be preferred.

The etching of Ir and $IrO_2$ in the practice of the invention, after the initial formation of the iridium-containing film, may be carried out with the use of halogen-based systems, such as chlorine, bromine, and fluorine based plasma or ion beam etch chemistries. The formation of halogens of Ir(I) and Ir(III) can be exploited to etch and pattern electrodes for semiconductor and ferroelectric device applications. In systems where $IrO_2$ is present, the use of either a reducing pre-treatment (to return the iridium oxide to Ir metal) or the use of fluorine etchants may be preferred. The formation and removal of etch by-products depends on the volatility of the halide species. The addition of stabilizing co-reactants may usefully be employed to facilitate the removal and etching of the materials.

The iridium-containing films deposited in accordance with the method of the present invention may be etched with a dry etch method, as more fully described in the aforementioned co-pending U.S. patent application Ser. No. 08/966,796 filed Nov. 10, 1997, optionally using specific chemical enhancements to the rate of etching. The addition of carbon monoxide, trifluorophosphine, or trialkyl phosphines can accelerate the rate of etching by enhancing the volatility of the produced etch by-products.

For example, in the etching of the Ir-containing film on the substrate, the removal rate for the process may be advantageously accelerated by the presence of carbon monoxide (CO). The rates are strongly dependent upon the gas-phase partial pressure of the reactants in elevated substrate temperature regimes (e.g., 725–975° C.). The presence of CO may serve to enhance the reactant volatility through the formation of $(CO)_y IrX_3$ (where X=Cl, Br) and for $Ir(Cl)_4$. $IrF_6$ may also be employed for such purpose. These materials can be used advantageously for etching Ir in halogen-based plasmas, ion beams and in hybrid etching schemes.

In some instances, it may be desirable to convert the iridium oxide material deposited on the substrate to a pure iridium metal for a specific fabrication or device application. In such instance, the deposited film of iridium oxide may be exposed to a reducing gas, such as hydrogen, forming gas, CO, ROH, etc. to effect such conversion.

After its formation and any additional patterning, the iridium-containing electrode may have deposited thereon a high temperature dielectric and/or ferroelectric material in the same oxidizing ambient environment employed for the deposition of the iridium-containing film.

It is therefore unnecessary to purge the chamber of a reducing atmosphere, or to transfer the substrate article bearing the iridium-containing film from the iridium deposition chamber to a dielectric/ferroelectric deposition chamber, as has been done in the prior art to accommodate the usage of hydrogen or other reducing gas (forming gas) atmospheres in the iridium electrode formation step. The method of the invention therefore achieves a substantial simplification of the procedure for forming a capacitor or other microelectronic device in which the iridium-containing electrode is overcoated with a dielectric or ferroelectric material.

The iridium films deposited in the practice of the present invention may therefore be utilized for the formation of electrode and other elements of semiconductor devices, such as for example DRAMs, FRAMs, hybrid systems, smart cards and communication systems, as well as any other applications in which the thin films of iridium and/or iridium oxide are advantageously employed, such as catalytic systems.

While the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A composition including an iridium source reagent selected from the group consisting of:

Lewis base stabilized Ir(I) β-diketonates of formula I:

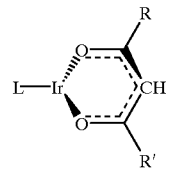

I wherein R and R' may be alike or different and may be H, aryl, perfluoroaryl, $C_1$–$C_6$ alkyl, or $C_1$–$C_6$ perfluoroalkyl; and L is a coordinating Lewis base; and Lewis base stabilized Ir(I) β-ketoiminates of formula II:

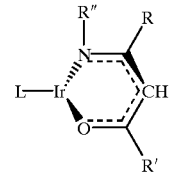

II wherein R, R', and R" are the same or different, and are independently selected from the group consisting of H, aryl, perfluoroaryl, $C_1$–$C_6$ alkyl, or $C_1$–$C_6$ perfluoroalkyl, and L is a coordinating Lewis base selected from the group consisting of alkene, diene, cycloalkene, cyclooctatetraene, alkyne, substituted alkyne (symmetrical or asymmetrical), amine, diamine, triamine, tetraamine, ether, diglyme, triglyme, tetraglyme, dialkyl sulfide, vinyltrimethylsilane, and allyltrimethylsilane.

2. A Lewis base stabilized Ir(I) β-diketonate of formula I:

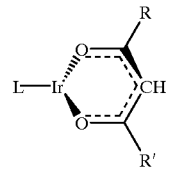

I wherein R and R' may be alike or different and may be H, aryl, perfluoroaryl, $C_1$–$C_6$ alkyl, or $C_1$–$C_6$ perfluoroalkyl, and L is a coordinating Lewis base selected from the group consisting of alkene, diene, cycloalkene, cyclooctatetraene, alkyne, substituted alkyne (symmetrical or asymmetrical), amine, diamine, triamine, tetraamine, ether, diglyme, triglyme, tetraglyme, dialkyl sulfide, vinyltrimethylsilane, and allyltrimethylsilane.

3. A Lewis base stabilized Ir(I) β-ketoiminate of formula II:

Lewis base stabilized Ir(I) β-diketonates of formula I:

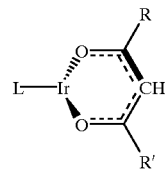

wherein R and R' may be alike or different and may be H, aryl, perfluoroaryl, $C_1$–$C_6$ alkyl, or $C_1$–$C_6$ perfluoroalkyl; and L is a coordinating Lewis base; and Lewis base stabilized Ir(I) β-ketoiminates of formula II:

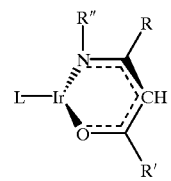

wherein R, R', and R" are the same or different, and are independently selected from the group consisting of H, aryl, perfluoroaryl, $C_1$–$C_6$ alkyl or $C_1$–$C_6$ perfluoroalkyl, and L is a coordinating Lewis base, wherein the Lewis base is selected from the group consisting of amine, diamine, triamine, tetraamine, ether, diglyme, triglyme, tetraglyme, vinyltrimethylsilane, and allyltrimethylsilane.

12. A composition according to claim 11, comprising the iridium source reagent in an organic solution.

13. A composition according to claim 12, wherein the iridium source reagent comprises a Lewis base stabilized Ir(I) β-diketonate of formula I.

14. A composition according to claim 8, wherein the iridium source reagent comprises a Lewis base stabilized Ir(I) β-ketoiminate of formula II.

* * * * *

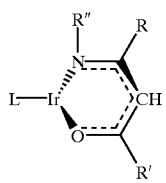

wherein R, R', and R" are the same or different, and are independently selected from the group consisting of H, aryl, perfluoroaryl, $C_1$–$C_6$ alkyl, or $C_1$–$C_6$ perfluoroalkyl, and L is a coordinating Lewis base selected from the group consisting of alkene, diene, cycloalkene, cyclodiene, cyclooctatetraene, alkyne, substituted alkyne (symmetrical or asynmmetrical), amine, diamine, triamine, tetraamine, ether, diglyme, triglyme, tetraglyme, phosphine, carbonyl, dialkyl sulfide, vinyltrimethylsilane, and allyltrimethylsilane.

4. A composition according to claim 1, comprising a Lewis base stabilized Ir(I) β-diketonate of formula I, wherein R and R' are each alkyl.

5. A composition according to claim 1, comprising a Lewis base stabilized Ir(I) β-diketonate of formula I, wherein R and R' are each perfluoroalkyl.

6. A composition according to claim 1, comprising a Lewis base stabilized Ir(I) β-ketoiminate of formula II, wherein R and R' are each alkyl.

7. A composition according to claim 1, comprising a Lewis base stabilized Ir(I) β-ketoiminate of formula II, wherein R and R' are each perfluoroalkyl.

8. A composition according to claim 1, comprising the iridium source reagent in an organic solution.

9. A composition according to claim 8, wherein the iridium source reagent comprises a Lewis base stabilized Ir(I) β-diketonate of formula I.

10. A composition according to claim 8, wherein the iridium source reagent comprises a Lewis base stabilized Ir(I) β-ketoiminate of formula II.

11. A composition including an iridium source reagent selected from the group consisting of:

UNITED STATES PATENT AND TRADEMARK OFFICE
CERTIFICATE OF CORRECTION

PATENT NO : 6,018,065

DATED : Jan. 25, 2000

INVENTOR(S) : Thomas H. Baum; Chong-Ying Xu

It is certified that error appears in the above-identified patent and that said Letters Patent are hereby corrected as shown below:

Title Page, [54], line 3: after "SUBSTRATES," insert --AND--.
Title Page, [57], line 2: change "contaiing" to --containing--.
Column 1, line 3: after "SUBSTRATES," insert --AND--.
Column 1, line 14: change "TV" to --The--.
Column 7, line 17: change "asynmmetrical" to --asymmetrical--.

Signed and Sealed this

Twenty-second Day of May, 2001

Attest:

NICHOLAS P. GODICI

Attesting Officer    *Acting Director of the United States Patent and Trademark Office*